(12) United States Patent
Hough

(10) Patent No.: US 7,648,175 B2
(45) Date of Patent: Jan. 19, 2010

(54) MEDICAL GAS OUTLET WITH SUPPORT BRACKET

(76) Inventor: Robert Hough, 9780 E. 600 South, Zionsville, IN (US) 46077

( * ) Notice: Subject to any disclaimer, the term of this patent is extended or adjusted under 35 U.S.C. 154(b) by 798 days.

(21) Appl. No.: 11/280,623

(22) Filed: Nov. 16, 2005

(65) Prior Publication Data

US 2007/0125426 A1   Jun. 7, 2007

(51) Int. Cl.
*F16L 5/00* (2006.01)
(52) U.S. Cl. .................. 285/24; 137/360; 137/329.4
(58) Field of Classification Search ................ 285/189, 285/24; 137/358, 359, 360, 361, 329.4
See application file for complete search history.

(56) References Cited

U.S. PATENT DOCUMENTS

| | | | | |
|---|---|---|---|---|
| 3,532,101 A | * | 10/1970 | Snyder, Jr | 137/75 |
| 3,544,257 A | * | 12/1970 | Cranage | 137/360 |
| 3,643,985 A | * | 2/1972 | Cranage | 285/189 |
| 4,344,455 A | * | 8/1982 | Norton et al. | 137/329.4 |
| 4,718,699 A | * | 1/1988 | Kulish et al. | 285/12 |
| 5,020,563 A | * | 6/1991 | Hoffman et al. | 137/75 |
| 5,197,511 A | * | 3/1993 | Kohn et al. | 137/360 |
| 5,236,005 A | * | 8/1993 | Berg | 137/360 |
| 5,562,121 A | * | 10/1996 | Hodges et al. | 285/24 |
| 6,945,511 B2 | * | 9/2005 | Schulze | 251/149.8 |

* cited by examiner

*Primary Examiner*—David E Bochna
(74) *Attorney, Agent, or Firm*—Harness, Dickey & Pierce, P.L.C.

(57) ABSTRACT

A support bracket is affixed to a medical gas outlet. The support bracket supports one or more elements of a gas circuit coupled to the medical gas outlet and prevents deformation of a lock spring of the medical gas outlet. The medical gas outlet can be a wall mounted vacuum or oxygen outlet.

9 Claims, 4 Drawing Sheets

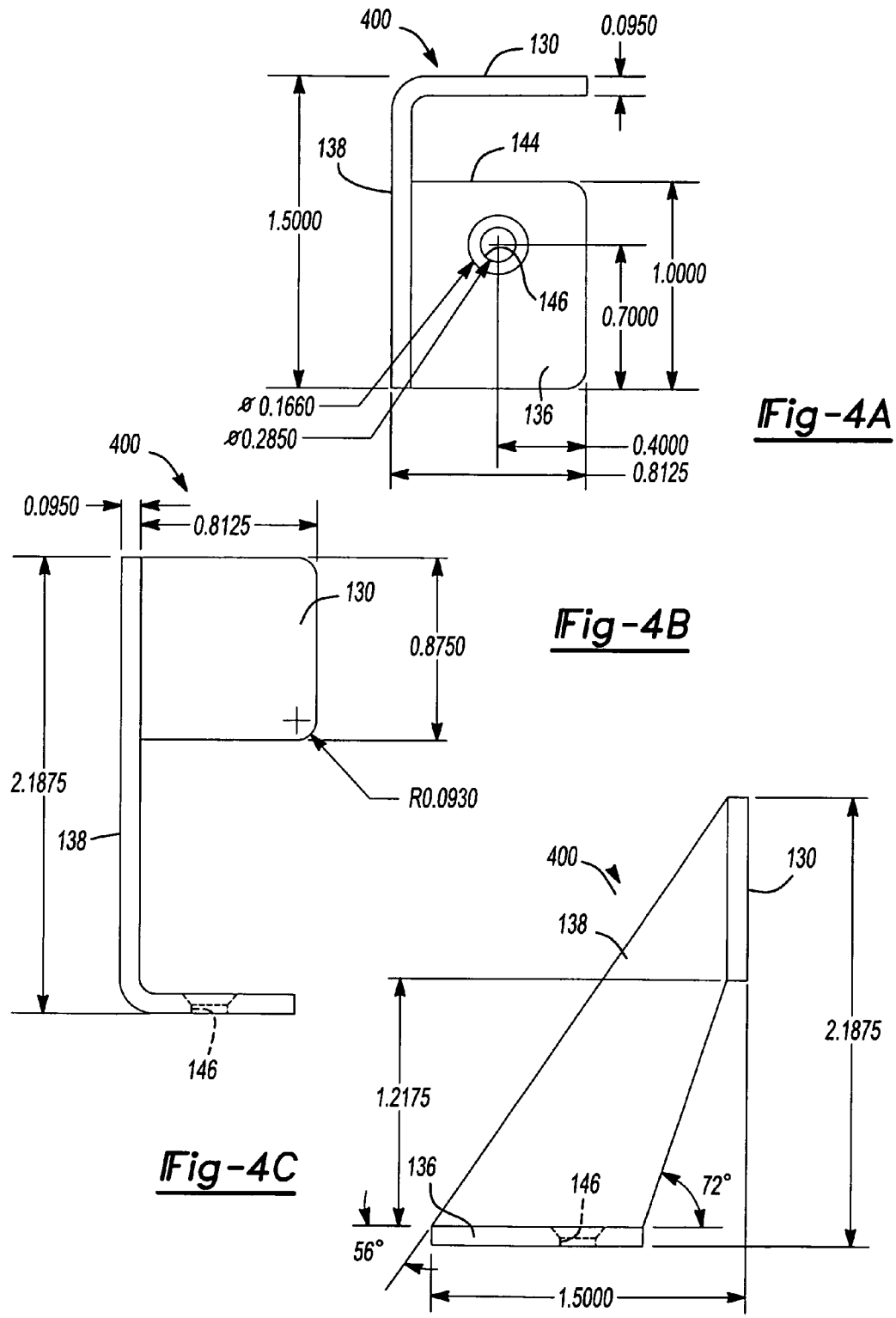

MEDICAL GAS OUTLET WITH SUPPORT BRACKET

FIELD OF THE INVENTION

The present invention relates to medical gas outlets, and in particular to medical oxygen and vacuum outlets disposed in walls of healthcare facilities and prevention of deformation of the lock springs of these outlets.

BACKGROUND OF THE INVENTION

In medical facilities, such as hospital rooms, medical gas outlets are disposed in walls or columns of the rooms. The most typical medical gas outlets are oxygen and vacuum outlets. Each outlet is coupled to a source of the medical gas, such as to a pipe that runs within the walls or columns of the healthcare facility to the medical gas source. In the case of an oxygen outlet, the oxygen outlet is coupled to a source of oxygen. In the case of a vacuum outlet, the vacuum outlet is coupled to a source of vacuum. (Although in the case of vacuum, the outlet is actually an inlet, it is still typically referred to as a vacuum outlet.)

A typical wall mount medical gas outlet has a port, such as a cylinder, into which a quick connect of a gas circuit is plugged. An example of a typical wall mount is a Diamond III Recess Wall Mount available from BeaconMedaes of 13325-A Carowinds Blvd Charlotte, N.C. 28273. The quick connect, which has a hollow passage, connects the gas circuit to the source of medical gas when the quick connect is plugged into the outlet. A gas circuit has various elements depending on the application. For example, if a patient is on oxygen, the oxygen gas circuit may include a patient face mask that is placed over the nose and mouth of the patient. The mask is connected by tubing to the oxygen flow meter that is plugged into an oxygen outlet. The gas circuit may also include valves that appropriately direct the flow of the oxygen and air exhaled by the patient as the patient inhales and exhales, as well as filter(s), regulator(s), etc.

The quick connect of the gas circuit typically includes a grooved end. The gas outlet includes a lock spring, such as in the form of a U-shaped clip spring that clips around the grooved end of the quick connect when the quick connect of the gas regulator or flow meter, etc. is plugged into the outlet. The lock spring locks the quick connect in the outlet and prevents it from being removed from the outlet unless the lock spring is "unlocked." That is, when the lock spring is a U-shaped clip spring, the legs of the lock spring must be urged apart so that the quick connect can be removed from the outlet. This is typically accomplished by rotating a keying disc of a keying disc assembly that holds the lock spring. The keying disc has one or more cam surfaces or ears that urge the legs of the lock spring apart when the keying disc is rotated, allowing the plug of the gas circuit to be removed from the gas outlet.

Since the typical medical gas outlet is relatively small, the lock spring is also relatively small. For example, the port of a typical medical gas outlet has an inside diameter of 17 mm. If force is applied to the quick connect of the gas circuit transverse to the axis of the quick connect, this force will cause a "lever" action of the quick connect against the lock spring. If the force is high enough, the "lever" action of the quick connect of the gas circuit against the lock spring will deform the lock spring. This will make it more difficult if not impossible to unlock the lock spring. That is, the lock spring may be sufficiently deformed that the keying disc cannot be rotated to unlock it. When this occurs, the gas outlet must be disassembled to both to remove the quick connect of the gas circuit from the gas outlet and to repair the gas outlet.

In many cases, heavier elements of the gas circuit are disposed in close proximity to the quick connect, or may even include the quick connect. Such elements may include an oxygen flow meter, suction regulator, air flow meter or Y connector. (used for dual elements to be connected to one gas outlet). In these cases, the weight of the elements of the gas circuit apply some amount of transverse force to the quick connect of the gas circuit. This may itself eventually deform the lock spring, or make it more likely that the lock spring will be deformed if the gas circuit is inadvertently bumped or force otherwise applied to it.

SUMMARY OF THE INVENTION

In accordance with the invention, a support bracket is affixed to a medical gas outlet. The support bracket supports one or more elements of a gas circuit coupled to the medical gas outlet and prevents deformation of a lock spring of the medical gas outlet. In an aspect, the medical gas outlet is a wall mounted medical gas outlet. In an aspect, a medical gas outlet assembly has a medical gas outlet and a support bracket extending from the medical gas outlet. The support bracket has a support flange disposed below an opening of a port of the medical gas outlet. The support flange supports one or more elements of a gas circuit when the gas circuit is coupled to the medical gas outlet and prevents deformation of a lock spring of the medical gas outlet. In an aspect, the medical gas outlet is an oxygen outlet. In an aspect, the medical gas outlet is a vacuum outlet.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 4A is front view of a support bracket for a vacuum outlet in accordance with an aspect of the invention;

FIG. 4B is a bottom view of the support bracket of FIG. 4A; and

FIG. 4C is a side view of the support bracket of FIG. 4A.

DETAILED DESCRIPTION OF THE PREFERRED EMBODIMENTS

The following description of the preferred embodiment(s) is merely exemplary in nature and is in no way intended to limit the invention, its application, or uses.

Figure 1:
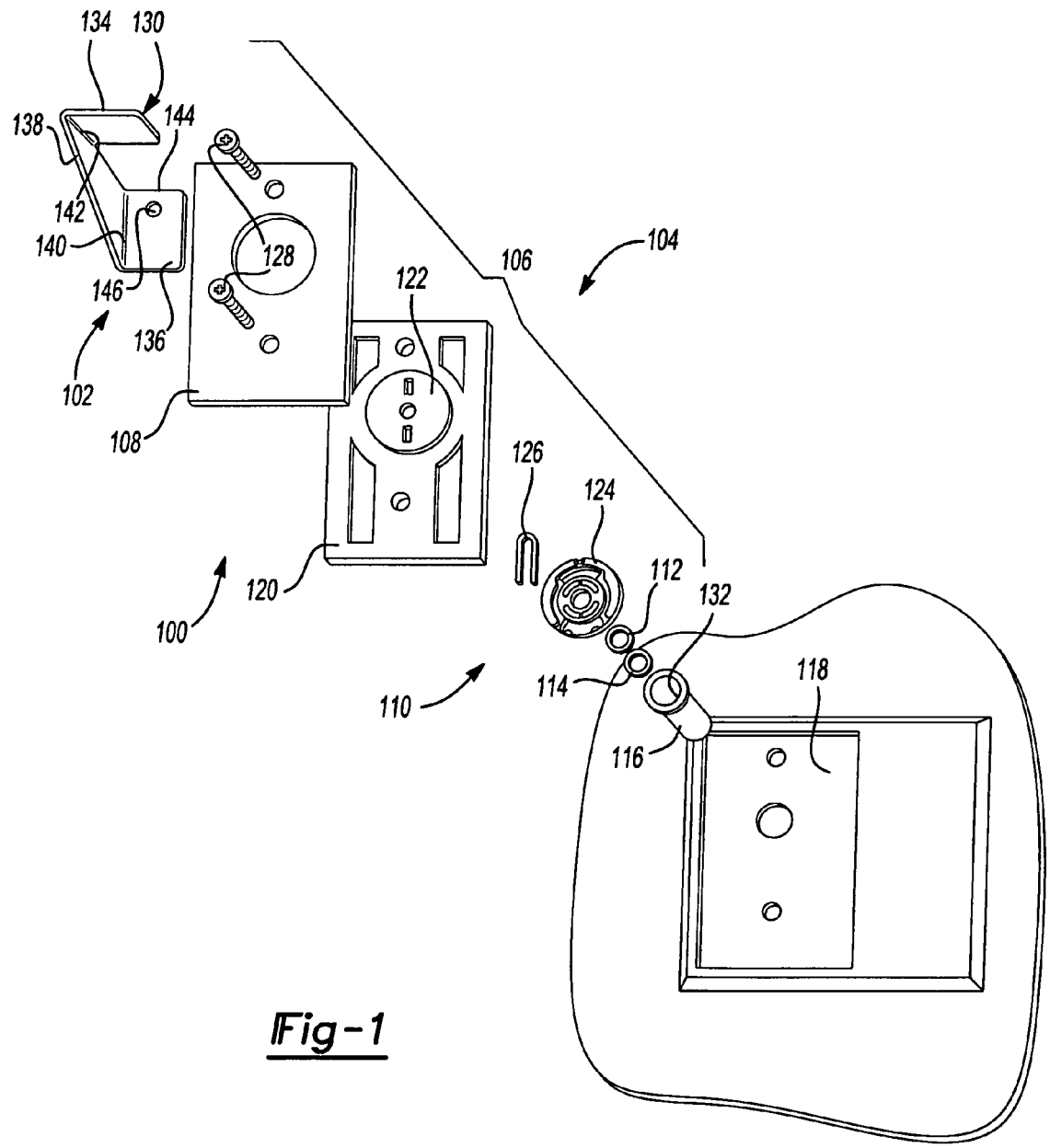
FIG. 1 is a an exploded view of a medical gas outlet assembly having a support bracket in accordance with an aspect of the invention.
Figure 2:
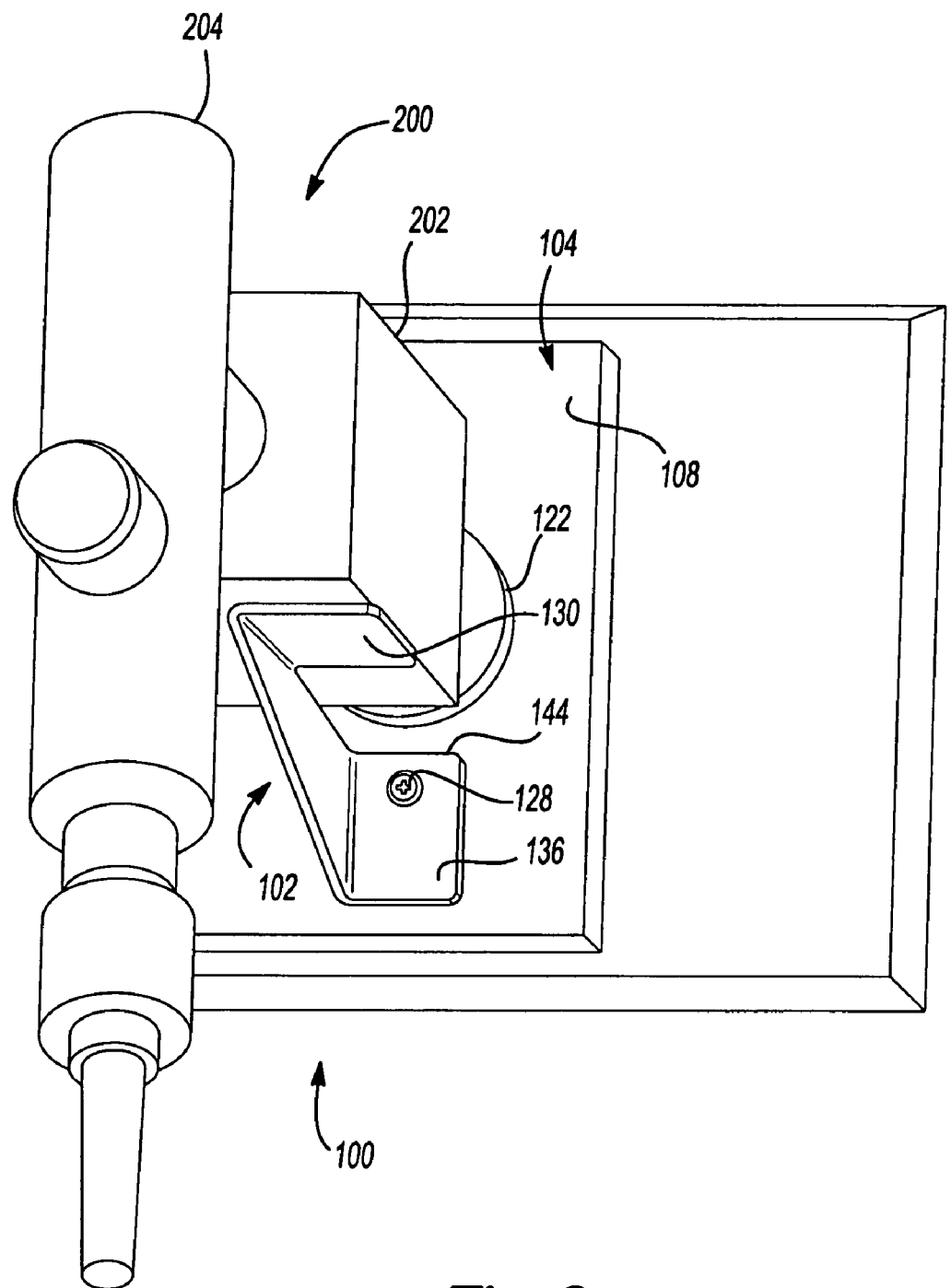
FIG. 2 is a front plan view of a medical gas outlet assembly of FIG. 1 with a gas circuit coupled to the medical gas outlet.

FIGS. 1 and 2 show a medical gas outlet assembly 100 in accordance with the invention. Medical gas outlet assembly 100 includes a support bracket 102 and a medical gas outlet 104. Medical gas outlet 104 is illustratively a typical wall mounted medical gas outlet of the type described above. FIG. 1 shows that part of medical gas outlet 104 sometimes referred to as the finishing assembly (identified by reference number 106). Medical gas outlet 104 further includes what is sometimes referred to as a roughing-in assembly, not shown in FIG. 1, to which the finishing assembly 106 is attached. Roughing-in assembly typically includes a back plate, comparable to an electrical junction box, that is affixed within a wall of a healthcare facility, such as to wall studs. Medical gas outlet 104 includes a face of finish plate 108, keying disc assembly 110, washer 112, O-ring 114, cylinder or port 116 and cover plate 118.

Keying disc assembly 110 includes plate 120 in which keying disc 122 is rotatably disposed and check body 124 in which lock spring 126 is disposed. Face plate 108, plate 120 of keying disc assembly and cover plate 118 are secured to the back plate (not shown) of the roughing-in assembly (not shown) of medical gas outlet 104, such as with screws 128.

Support bracket 102 is affixed to medical gas outlet 104 and includes a horizontally (as oriented in FIGS. 1 and 2) extending support flange 130 disposed beneath an opening 132 of cylinder or port 116 of medical gas outlet 104. A top 134 of support flange 130 is in proximity to but slightly beneath opening 132 of cylinder or port 116 a sufficient distance to allow the quick connect of the gas circuit to be easily inserted into cylinder or port 116 yet sufficiently close to opening 132 so as to support the quick connect (not shown) of gas circuit 200 (FIG. 2) and any accompanying element of the gas circuit that is in close proximity to the quick connect of the gas circuit. For example, as illustratively shown in FIG. 2, gas circuit 200 includes a first element 202, which illustratively includes the quick connect (not shown) of the gas circuit. Gas circuit 200 further includes second element 204 coupled to a side of first element 202 distal from medical gas outlet 104. First element 202 of gas circuit 200 is supported on support flange 130 of support bracket 102 and prevents the plug of the gas circuit from "levering" against lock spring 126, preventing deformation of lock spring 126.

In the embodiment shown in FIGS. 1 and 2, support bracket 102 includes vertical mounting flange 136 having an arm 138 extending outwardly and upwardly from side 140 of vertical mounting flange 136. Support flange 130 extends transversely from a top 142 of arm 138. Vertical mounting flange 136 includes a screw hole 146. Support bracket 102 is then affixed to medical gas outlet 104 by one of screws 128 that is also used to secure face plate 108, plate 120 of keying disc assembly 110, and cover plate 118 to the back plate or junction box of the roughing-in assembly (not shown). Support flange 130 is illustratively spaced above a top 144 of vertical mounting flange 136 of support bracket 102 to provide adequate clearance between top 144 of vertical mounting flange 136 and a bottom of keying disc 122 of medical gas outlet 104. As is known and is shown in FIG. 2, keying disc 122 projects outwardly from face plate 108 so that a user can grasp and rotate keying disc 122 to unlock lock spring 126.

Support bracket 102 may illustratively be formed as a single piece, such as by stamping it from steel. It may also illustratively be formed by molding it, such as by injection molding it of plastic. In the embodiment shown in FIGS. 1 and 2, support bracket 102 is a separate part that is affixed to medical gas outlet 104 with one of screws 128, which permits existing installations of medical gas outlets 104 to be easily retrofitted with support brackets 102. It should be understood, however, that support bracket 102 could be formed as part of another part of medical gas outlet 104, such as being formed as part of face plate 108.

Figure 3A:
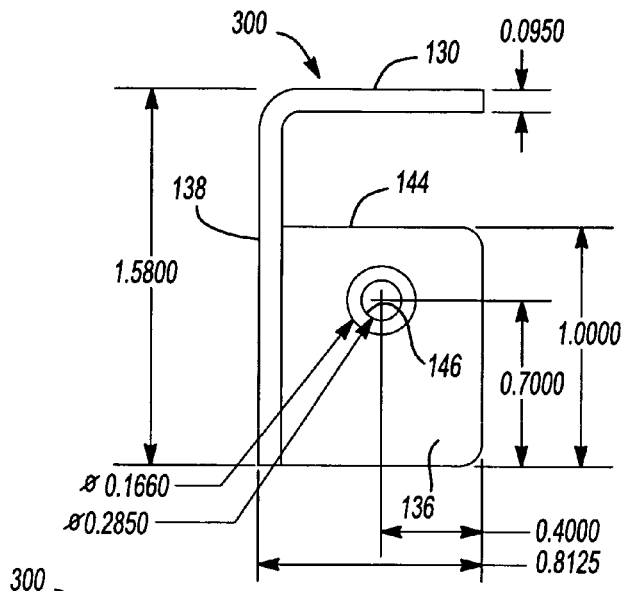
FIG. 3A is front view of a support bracket for an oxygen outlet in accordance with an aspect of the invention.
Figure 3B:
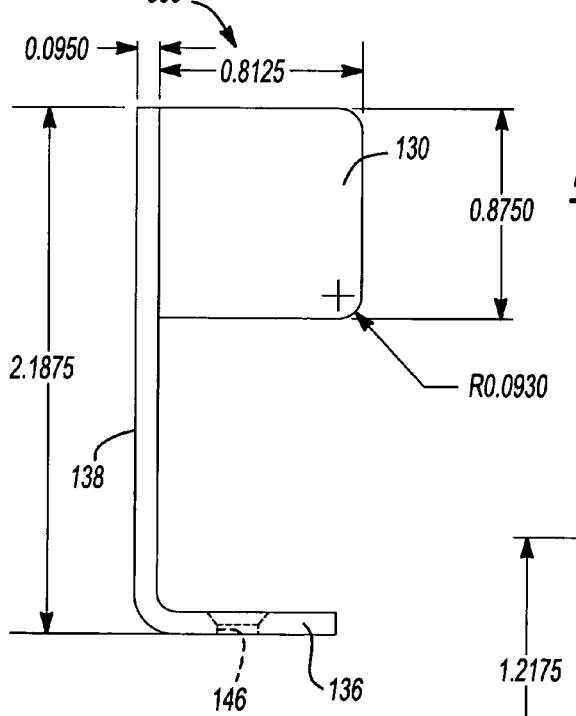
FIG. 3B is a bottom view of the support bracket of FIG. 3A.
Figure 3C:
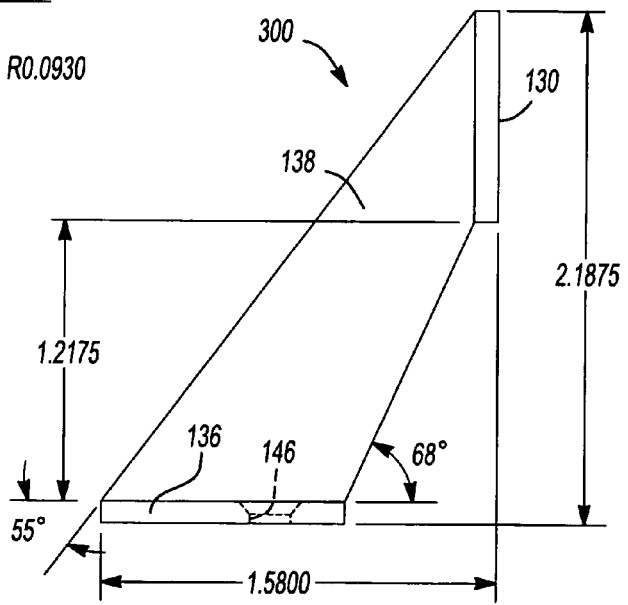
FIG. 3C is a side view of the support bracket of FIG. 3A.

FIGS. 3A-3C and 4A-4C show in more detail two variations of support bracket 102, support bracket 300 shown in FIGS. 3A-3C for use with an oxygen outlet and support bracket 400 shown in FIGS. 4A-4C for use with a vacuum outlet. (Dimensions are in inches.) Elements in common with FIGS. 1 and 2 will be identified with the same reference numbers. Supports brackets 300, 400 are essentially identical, the only difference being the distance which support flange 130 is spaced above top 144 of vertical mounting flange 136. Since the elements of a vacuum circuit that are in close proximity to the plug of the circuit tend to be somewhat larger than elements of an oxygen circuit that are in close proximity to the plug of the circuit, the distance that support flange 130 of oxygen outlet support bracket 300 is spaced above top 144 of vertical mounting flange 136 is slightly greater than the distance that support flange 130 of vacuum outlet support bracket 400 is spaced above top 144 of vertical mounting flange. 136.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method of preventing deformation of a lock spring of a medical gas outlet having a port that removably receives a quick connect of a gas circuit that engages the lock spring when received in the port, comprising affixing a support bracket to the medical gas outlet that has a support flange disposed beneath the port of the medical gas outlet which supports at least one element of the gas circuit disposed outwardly of the port when the quick connect of the gas circuit is removably received in the port of the gas outlet and prevents deformation of the lock spring.

2. The method of claim 1 wherein affixing the support bracket to the medical gas outlet includes affixing it with a screw that also secures a face plate of the medical gas outlet to another part of the medical gas outlet.

3. The method of claim 1 wherein the medical gas outlet is one of an oxygen outlet and a vacuum outlet.

4. A medical gas outlet assembly, comprising:
   a. a medical gas outlet having a lock spring disposed therein that engages a quick connect of a gas circuit when the quick connect is removably received in a port of the medical gas outlet; and
   b. a support bracket extending from the medical gas outlet, the support bracket having a support flange disposed below an opening of the port of the medical gas outlet and extending outwardly from the port, the support flange supporting an element of the gas circuit when the quick connect of the gas circuit is removably received in the port of the medical gas outlet and prevents deformation of the lock spring of the medical gas outlet.

5. The assembly of claim 4 wherein the support bracket includes a mounting flange having a screw hole therein through which a screw of the medical gas outlet is received to secure the support bracket to the medical gas outlet.

6. The assembly of claim 4 wherein the support bracket includes a mounting flange having an outwardly and upwardly extending arm, the support flange extending transversely from a top of the arm.

7. The assembly of claim 6 wherein the mounting flange includes a screw hole therein through which a screw of the medical gas outlet is received to affix the support bracket to the medical gas outlet.

8. The assembly of claim 4 wherein the support flange extends horizontally outwardly from the medical gas outlet below the opening of the port of the medical gas outlet.

9. The assembly of claim 4 wherein the medical gas outlet is one of an oxygen outlet and a vacuum outlet.

* * * * *

UNITED STATES PATENT AND TRADEMARK OFFICE
CERTIFICATE OF CORRECTION

PATENT NO. : 7,648,175 B2  
APPLICATION NO. : 11/280623  
DATED : January 19, 2010  
INVENTOR(S) : Robert Hough It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1099 days.

Signed and Sealed this

Sixteenth Day of November, 2010

David J. Kappos  
*Director of the United States Patent and Trademark Office*